(12) United States Patent
Carpentier

(10) Patent No.: US 7,700,569 B1
(45) Date of Patent: *Apr. 20, 2010

(54) USE OF STABILISED OLIGONUCLEOTIDES FOR PREPARING A MEDICINE WITH ANTITUMOR ACTIVITY

(75) Inventor: Antoine F. Carpentier, Paris (FR)

(73) Assignees: Assistance Publique-Hopitaux de Paris, Paris (FR); Institut National de la Sante Et de la Recherche Medicale, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/937,057

(22) PCT Filed: Mar. 17, 2000

(86) PCT No.: PCT/FR00/00676

§ 371 (c)(1),
(2), (4) Date: Feb. 26, 2002

(87) PCT Pub. No.: WO00/56342

PCT Pub. Date: Sep. 28, 2000

(30) Foreign Application Priority Data

Mar. 19, 1999 (FR) .................................. 99 03433

(51) Int. Cl.
| A61N 43/04 | (2006.01) |
| C12Q 1/68 | (2006.01) |
| C12P 19/34 | (2006.01) |
| C12N 15/63 | (2006.01) |
| C07H 21/02 | (2006.01) |

(52) U.S. Cl. .......................... 514/44; 435/6; 435/91.1; 435/455; 536/23.1

(58) Field of Classification Search ................ 435/6, 435/91.1, 455, 458; 514/1, 2, 44; 536/23.1, 536/24.1
See application file for complete search history.

(56) References Cited

U.S. PATENT DOCUMENTS

| 5,663,153 | A | 9/1997 | Hutcherson et al. |
| 5,723,335 | A | 3/1998 | Hutcherson et al. |
| 5,734,033 | A | 3/1998 | Reed |
| 6,001,982 | A | 12/1999 | Ravikumar et al. |
| 6,020,475 | A | 2/2000 | Capaldi et al. |
| 6,022,691 | A | 2/2000 | Bruice et al. |
| 6,069,243 | A | 5/2000 | Scozzari |
| 6,121,437 | A | 9/2000 | Guzaev et al. |
| 6,153,737 | A | 11/2000 | Manoharan et al. |
| 6,160,109 | A | 12/2000 | Just et al. |
| 6,160,152 | A | 12/2000 | Capaldi et al. |
| 6,165,766 | A * | 12/2000 | Creasy et al. ............. 435/194 |
| 6,166,239 | A | 12/2000 | Manoharan |
| 6,169,177 | B1 | 1/2001 | Manoharan |
| 6,194,388 | B1 | 2/2001 | Krieg et al. |
| 6,207,646 | B1 | 3/2001 | Krieg et al. |
| 6,218,371 | B1 * | 4/2001 | Krieg et al. ..................... 514/44 |
| 6,239,116 | B1 | 5/2001 | Krieg et al. |
| 6,280,978 | B1 * | 8/2001 | Mitchell et al. ............. 435/91.3 |
| 6,562,796 | B2 * | 5/2003 | Baldwin et al. ................ 514/31 |
| 6,562,798 | B1 * | 5/2003 | Schwartz ........................ 514/44 |
| 7,108,844 | B2 * | 9/2006 | Carpentier .................. 424/1.11 |

FOREIGN PATENT DOCUMENTS

| EP | 0 468 520 A2 | 7/1990 |
| EP | 0 855 184 A1 | 7/1998 |
| WO | WO 94/25588 | 11/1994 |
| WO | WO 96/02555 | 2/1996 |
| WO | WO 97/44346 | 11/1997 |
| WO | WO 98/18810 | 5/1998 |
| WO | WO 98/55495 | 12/1998 |
| WO | WO 99/12027 | 3/1999 |
| WO | WO 99/26634 | 6/1999 |
| WO | WO 99/51259 | 10/1999 |
| WO | WO 00/62923 | 12/1999 |
| WO | WO 00/16804 | 3/2000 |
| WO | WO 00/21556 | 4/2000 |

OTHER PUBLICATIONS

Chirila, T.V. et al., Biomaterials, vol. 23, pp. 321-342 (2002).*
Agrawal, S. et al., Molecular Med. Today, vol. 61, pp. 72-81 (2000).*
Clark, M. et al., WashU Zebrafish EST Project, Accession No. BI881470 (1998).*
Crooke, S.T., et al., Annu. Rev. Med., vol. 55, pp. 61-95 (2004).*
Peracchi, A. et al., Rev. Med. Virol., vol. 14, pp. 47-64 (2004).*
Chirila, T., et al., Biomaterials, vol. 23, pp. 321-324 (2002).*
Agrawal, S., et al., Molecular Med. Today, vol. 6, pp. 72-81 (2000).*
Opalinska, J.B., et al., Nature Rev., vol. 1, pp. 503-514 (2002).*
Branch, A., Trends in Biochem. Sci., vol. 23, pp. 45-50 (1998).*
Ballas, Zuhair K. et al., "Induction of NK Activity in Murine and Human Cells by CpG Motifs in Oligodeoxynucleotides and Bacterial DNA," J. of Immunol. 1996, 157: 1840-1845.
Ishizaka, Y. et al., "Human ret proto-oncogene mapped to chromosome 10q11.2," Nat'l Cancer Res. Instit. Aug. 17, 1989 (Short Report).
LaPlanche, Laurine A. et al., "Phosphorothioate-modified oligodeoxyribonucleotides, III, NMR and UV spectroscopic studies of the $R_p$-$R_p$, $S_p$-$S_p$, and $R_p S_p$, duplexes, [d($GG_8$AATTCC)]$_2$, derived from diastereomeric 0-ethyl phosphorothioates," Nucleic Acids Research, vol. 14, No. 22, 1986 pp. 9081-9093.
Liang, Hua et al., "Activation of Human B Cells by Phosphorothioate Oligodeoxynucleotides," J. Clin. Invest. vol. 98,No. 5, Sep. 1996, pp. 1119-1129.
Lipford, Grayson B. et al., "CpG-containing synthetic oligonucleotides promote B and cytotoxic T cell responses to protein antigen: a new class of vaccine adjuvants," Eur. J. Immunol. 1997, 27:2340-2344.

(Continued)

Primary Examiner—Jane Zara
(74) Attorney, Agent, or Firm—Oblon, Spivak, McClelland, Maier & Neustadt, L.L.P.

(57) ABSTRACT

The invention concerns the use of stabilized oligonucleotides comprising at least an octamer motif of the type: 5'-purine-purine-CG-pyrimdine-pyrimidine-$X_1 X_2$-3' wherein the pair $X_1$-$X_2$ is AT, AA, CT or TT, for preparing a medicine with antitumour activity.

17 Claims, 11 Drawing Sheets

OTHER PUBLICATIONS

Pirotton, Sabine et al., "Adenine Nucleotides Modulate Phosphatidylcholine Metabolism in Aortic Endothelial Cells," J. or Cellular Physiol. 142:449-457 (1990).

Rodgers, Kathy E. et al., "Investigations into the Mechanism of Immunosuppression Caused by Acute Treatment with *O,O,S*-Trimethyl Phosphorothioate: Generation of Suppressive Macrophages from Treated Animals," Toxicol. And Applied Pharmacol. 88, 270-281 (1987).

Ross, Peter et al., "The Cyclic Diguanylic Acid Regulatory System of Cellulose Synthesis in *Acetobacter xylinum*," J. of Biol. Chem. vol. 265, Issue of Nov. 5 pp. 18933-18943, 1990.

Connell Y.S. et al., "Anti-tumor activity of a CpG-containing oligodeoxynucleotide (ODN) in athymic mice," Proceedings of the American Association for Cancer Research Annual Meeting, Mar. 1999, vol. 40, p. 299.

US 6,008,200, 12/1999, Krieg (withdrawn)

\* cited by examiner

USE OF STABILISED OLIGONUCLEOTIDES FOR PREPARING A MEDICINE WITH ANTITUMOR ACTIVITY

The present invention relates to the use of stabilized oligonucleotides for preparing a medicament with antitumor activity.

The effective treatment of cancers remains one of the major challenges of medicine today.

The effectiveness of conventional surgical therapies or therapies aimed at cytolysis (chemotherapy and radiotherapy) remains very limited in many cancers.

For astrocytomas for example, the treatment of which is based mainly on surgical exeresis and local cerebral irradiation, the survival median is only 4 to 6 months after surgical exeresis and 8 to 10 months with the combination of surgery and radiotherapy. Supplementary chemotherapy prolongs survival in patients under the age of 60, but very modestly, by about 3 months. Under this triple treatment, the survival median remains less than two years for histological grade III (anaplastic astrocytoma) and less than 1 year for grade IV (glioblastoma). The mortality for these two groups is 100% (Daumas-Duport C. et al. (1988), *Cancer* 62(10) pp 2152-65).

Stimulation of the immune system in the treatment of cancers is a long-standing idea, and very many products have been tested, such as for example bacterial extracts (Jaeckle K. A. et al. (1990), *J. Clin. Oncol.* 8 (8) pp 1408-18) or bacterial DNA, in particular that of *Mycobacterium bovis* (MY-1) (Tokunaga T. et al. (1984), *JNCI* 72 pp 955-62). MY-1 is, however, ineffective in increasing survival in a model of glioma in mice (Nakaichi M. et al. (1995), *J. Vet. Med. Sci.* 57 (3) pp 583-5). IL2 (Herrlinger U. et al. (1996), *J. Neurooncol.* 27(3) pp 193-203) and, more recently, IL12 (Kishima H. et al. (1998), *Br. J. Cancer* 78(4) pp 446-53; Jean W. C. et al. (1998), *Neurosurgery* 42(4) pp 850-6) have also been studied.

Unfortunately, most of these products have a limited effectiveness or unacceptable toxicity and, to date, only the *Mycobacterium bovis* BCG has resulted in clinical applications, but only in very limited indications for bladder cancers (Soloway M. S. et al. (1988), *Urol. Clin. North Am.* 15 pp 661-9).

Oligonucleotides are polymers formed by the combination of purine or pyrimidine bases and of sugars, in particular ribonucleotides or deoxyribonucleotides. In the natural form, the linkages are phosphoester linkages which are sensitive to the nucleases of the human body. Thus, oligonucleotides have a very short half-life (of about one minute) when they are injected into humans, which limits their biological effects. Thus, several studies sought to stabilize oligonucleotides by modifying their chemical structure in order to make them resistant to nucleases. Several types of stabilized oligonucleotide have thus been created, such as, inter alia, phosphorothioates or methylphosphonates (Crooke R. M. (1991), *Anti-Cancer Drug Design* 6 pp 609-46). The most commonly used are phosphorothioate oligonucleotides.

Some oligodeoxynucleotides, and in particular some synthetic oligodeoxynucleotides, sometimes have biological effects per se, outside their conventional antisense properties.

Thus, some oligodeoxynucleotides, independently of any known antisense sequence, stimulate, in vitro and in vivo, the proliferation of B lymphocytes and the activity of NK cells, and induce the secretion by the cells of α-IFN, β-IFN, γ-IFN, IL6, IL12 or TNF-α (Yamamoto S. et al. (1992), *J. Immunol.* 148(12) pp 4072-6; Yamamoto T. et al. (1994), *Microbiol. Immunol.* 38(10), pp 831-6; Yi A. K. et al. (1996), *J. Immunol.* 157(12) pp 5394-402; Ballas Z. K. et al. (1996), *J. Immunol.* 157(5) pp 1840-5; Cowdery J. S. et al. (1996), *J. Immunol.* 156(12) pp 4570-5; Stacey K. J. et al. (1996), *J. Immunol.* 157(5) pp 2116-22). This set of cytokines direct toward a Th1-type immune response (Chu R. S. et al. (1997), *J. Exp. Med.* 186(10) pp 1623-31).

Authors have shown that the immunostimulatory properties of these oligodeoxynucleotides are in large part dependent on nonmethylated CG motifs (nonmethylated CpG dinucleotides) which are under-represented in mammalian DNA (Kuramoto E. et al. (1992), *Jpn. J. Cancer Res.*, 83 pp 1128-31).

While the authors agree on the fact that the nonmethylated CG sequence is essential and that the two nucleotides adjacent to the CG motif are also crucial for the immunostimulatory activity, the data published on the nature of the adjacent sequences are contradictory.

Specifically, Krieg A. M. et al. ((1996), *Antisense Nucleic Acid Drug Dev.* 6(2) pp 133-9) claim a hexameric motif of the type 5' purine purine CG pyrimidine pyrimidine 3', whereas application EP 468 520 claims a palindromic hexameric motif. International application WO 9855495 shows that not all the hexamers as defined by Krieg et al. 1996 (mentioned above) are immunostimulatory, and that octamers, of sequence 5'-purine purine CG pyrimidine pyrimidine CC-3' or of sequence 5'-purine purine CG pyrimidine pyrimidine CG-3' should rather be defined, in order to have immunostimulatory activity.

Other immunostimulatory oligodeoxynucleotides, which are not defined as oligonucleotides having a nonmethylated CG motif, have been described in application EP 855 184; they comprise the binding sequence for eukaryotic transcription factors such as NFκB or the AP-1 family. Among these oligonucleotides, some comprise the nonmethylated CG motif, however.

The use of the immunostimulatory properties of oligodeoxynucleotides comprising a nonmethylated CG-type motif is the subject of research in very varied domains:

(1) in the domain of vaccination, they are used, in combination with the antigen, as an adjuvant for stimulating specifically a Th1-type immune response (Davis H. L. et al. (1998), *The Journal of Immunology* 160(2) pp 870-6; application EP 855 184; international application WO 98/18810 in the name of The University of Iowa Research Foundation, of which A. M. Krieg is one of the inventors; international application WO 98/55495);

(2) in the domain of allergy, they are used alone for modulating the immune response (international applications WO 98/18810 and WO 98/55495) and (3) in the domain of cancer, they are used:
either in combination with a tumor antigen, as an adjuvant of an antitumor vaccine (application EP 855 184; Weiner G. J. et al. (1996), *Proc. Natl. Acad. Sci.* 94, pp 10833-7; Wooldridge J. E. et al. (1997) *Blood* 89(8) pp 2994-8),
or alone as antitumor agents (Connell et al. (1999), *Proceedings of the American association for Cancer Research* 40 pp 299; application EP 468 520; Carpentier A. F. et al. (1999), *Cancer Research* 59, pp 5429-5432.

In the latter case, the antitumor activity of only a few sequences, among those described, has been effectively demonstrated:

Weiner G. J. et al. and Wooldridge J. E. et al. (already cited) who use an oligonucleotide comprising a nonmethylated CG motif of sequence 5'-TCTCCCAGCGTGCGCCAT-3', show that this oligonucleotide has no antitumor effect when it is used alone;

Carpentier et al., Tokunaga et al. and Connell et al. (mentioned above), who use a phosphorothiate oligonucleotide of the octameric type (5'TGACTGTGAACGTTC- GAGATGA3'), a nonstabilized palindromic hexameric oligonucleotide (5' ACCGAT GACGTCGCCCGT-GACGGCACCACGACGAGGGCCACGTGCT 3') and a hexameric phosphorothioate oligonucleotide of the type 5' purine purine CG pyrimidine pyrimidine 3', respectively, show that said oligonucleotides have antitumor activity.

It emerges from the prior art that, other than the nonmethylated CG motif, the exact nature of the active sequences of these immunostimulatory oligodeoxynucleotides, for producing antitumor activity, is not clearly defined; in particular, the data published on the nature of the sequences adjacent to the nonmethylated CG motif (2 bases in 5' and 2 bases in 3' (hexameric motifs) or 4 bases in 3' (octameric motif)) are contradictory.

Recent studies reported by Hartmann G. et al. ((2000), *The Journal of Immunology* 164 pp 1617-24) give explanations concerning the difficulty in defining the sequence of such oligonucleotides.

Specifically, the authors show that, according to the nature of their sequence, the immunostimulatory oligodeoxynucleotides have differential effects on NK activation, the proliferation of B lymphocytes and the secretion of IL12, of IL6 and of γ-INF.

These data indicate that not all immunostimulatory oligodeoxynucleotides are equivalent and effective for all the uses as defined above since it is necessary to stimulate different compartments of the immune system in order to obtain the desired activity: adjuvant, antiallergic or antitumor activity.

In addition, the immune mechanisms of tumor rejection are poorly understood and the data for stimulation of the compartments of the immune system, in vitro, as defined above do not make it possible to predict in advance the antitumor effectiveness of a given oligonucleotide, and it is therefore important to test their antitumor activity in vivo.

Furthermore, the toxicity of oligodeoxynucleotides containing a CG-type motif has been reported when they are used systemically (IV and IP) and is also to be taken into account for therapeutic applications (application EP 855 184).

Consequently, the immunostimulatory oligo-nucleotides comprising a CG motif of the prior art (palindromic hexameric motif, motif 5' purine purine CG pyrimidine pyrimidine 3' or octameric motif), which have varying and random antitumor activities and are toxic, do not make it possible to define a set of effective nontoxic immunostimulatory sequences for antitumor use.

Now, the inventors have shown, surprisingly, that certain pairs of bases in 3' of the motif 5' purine purine CG pyrimidine pyrimidine 3' participate, in an essential way, in optimum antitumor activity.

Consequently, the inventors gave themselves the aim of providing a set of immunostimulatory oligonucleotide sequences which better satisfy practical needs in that they:
have optimum antitumor activity,
are not toxic and
are suitable for antitumor use in humans or animals.

Thus, the subject of the present invention is the use of stabilized oligonucleotides which comprise at least one octameric motif of the type 5'-purine-purine-CG-pyrimidine-pyrimidine-$X_1X_2$-3', in which the pair $X_1X_2$ is AT, AA, CT or TT, for preparing a medicament with antitumor activity.

For the purpose of the present invention, the term "oligonucleotide" is intended to mean an oligodeoxynucleotide.

According to a preferred embodiment of the invention, the stabilized oligonucleotides comprise at least one octameric motif selected from the group consisting of: AACGTT-$X_1X_2$, GACGTT-$X_1X_2$, AGCGTT-$X_1X_2$, GGCGTT-$X_1X_2$, AACGTC-$X_1X_2$, GACGTC-$X_1X_2$, AGCGTC-$X_1X_2$ and GGCGTC-$X_1X_2$ in which $X_1X_2$ is AT, AA, CT or TT.

According to an advantageous arrangement of this preferred embodiment of the invention, the stabilized oligonucleotides preferably comprise at least one of the following octameric motifs: AACGTT-$X_1X_2$ and GACGTC-$X_1X_2$.

In another preferred embodiment of the invention, one at least of the bases of the octameric motif described above can be modified, in particular one at least of the cytosines can be replaced with a 5-bromocytosine.

In another preferred embodiment of the invention, the stabilized oligonucleotide is selected from the group consisting of the sequences SEQ ID NO: 8 to 48.

In accordance with the invention, the stabilized oligonucleotides are selected in particular from the group consisting of phosphorothioate oligonucleotides, phosphorodithioate oligonucleotides, phosphodiester-phosphorothioate mixed oligonucleotides, methylphosphonate oligonucleotides and the oligo-nucleotides of which at least one end has been stabilized (Crooke R. M. (1991), *AntiCancer Drug Design*, 6 pp 609-46). Preferably, the stabilized oligonucleotides used according to the present invention are phosphorothioates.

In accordance with the invention, the stabilized oligonucleotides can be used in single-stranded or double-stranded form.

Preferably, the stabilized oligonucleotides can be any length longer than 8 bases or 8 base pairs, preferably more than 20 bases or more than 20 base pairs. Preferably, said oligonucleotides comprise between 20 and 100 nucleotides.

In accordance with the present invention, the oligonucleotides can comprise several octameric motifs as defined above, which may or may not be adjacent; they can also comprise other biologically active sequences, such as antisense sequences. The octameric sequences can themselves be included in antisense sequences.

A subject of the present invention is also the use of the stabilized oligonucleotides as defined above, for preparing medicaments intended for the treatment of cancers in humans, whatever their nature and their degree of anaplasia, in particular cancers of the central and peripheral nervous systems, especially astrocytomas, glioblastomas, medulloblastomas, neuroblastomas, melanomas and carcinomas.

The stabilized oligonucleotides can advantageously be coupled, via covalent, ionic or weak attachments, to a molecule capable of increasing tumor affinity, such as for example an antibody specific for the tumor tissue.

The stabilized oligonucleotides are preferably used via the intratumoral route, but they can also be administered via any other routes, optionally via multiple routes, in particular via the intravenous, intraperitoneal, topical, transdermal, subcutaneous, intra-arterial, pulmonary, nasopharyngeal or oral routes, in solution, in aqueous or oily suspension, as a powder or in any pharmaceutically acceptable form.

They can be administered in one or more doses, or in continuous release, in particular by means of osmotic micropumps, or combined with any physical or chemical means, especially with encapsulating agents such as colloidal dispersion systems and polymers, in order to have a therapeutically effective dose at the tumor site.

Effective doses will be determined as a function of the age, the state of health and the weight of the patient, and of the type of cancer to be treated. Typically, effective doses in humans are such that, in the case of an intratumoral injection, an oligonucleotide dose of 10 to 1000 μg/g of tumor is obtained at least in a part of the tumor.

In accordance with the invention, the use of the oligonucleotides can be combined with other therapies, in particular surgery, radiotherapy, chemotherapy, immunotherapy and differentiating therapies.

Also in accordance with the invention, said oligonucleotides are combined with cells of the immune system, such as macrophages, lymphocytes or antigen-presenting cells, adjuvants of immunity, cytokines, antitumor antibodies, tumor extracts, tumor antigens, or irradiated, genetically modified, or normal, tumor cells.

Besides the arrangements above, the invention also comprises other arrangements, which will emerge from the following description, which refers to the examples of implementation of the use, which is the subject of the present invention, and to the appended drawings in which:

FIG. 1 illustrates the results obtained after an intratumoral injection of the phosphorothioate oligodeoxynucleotide PT1 (SEQ ID NO: 2 5'-TGACTGTGAACGTTCGAGATGA-3'), in the glioma model CNS1 in the brain of Lewis rats (Kruse C. A. et al. (1994), *J. Neurooncol.* 22 pp 191-200), on the survival time of the control animals (–); PT1 50 μg injected at D1 (-.-.-.), PT1 50 μg injected at D5 (. . . .) and PT1 50 μg injected at D9 (- - -), after the injection of the tumor cells. The statistical analysis of the results is carried out using the Kaplan-Meier test.

FIG. 2 illustrates the effect of an intratumoral injection on D1 of the phosphorothioate oligodeoxynucleotide PT1 (SEQ ID NO: 2 5'-TGACTGTGAACGTTCGAGATGA-3'), at various doses, in the glioma model CNS1 of Lewis rats, on the survival time of the control animals (-); PT1 50 μg (- - - -), PT1 10 μg (-.-.-.) and PT1 1 μg ( . . . ).

FIG. 3 illustrates the effect of an intratumoral injection of the phosphorothioate oligodeoxynucleotide PT1 (SEQ ID NO: 2 5'-TGACTGTGAACGTTCGAGATGA-3') or of the phosphorothioate oligodeoxynucleotide IMM (SEQ ID NO: 1 5'-TGACTGTGAAGGTTAGAGATGA-3'), in a subcutaneous glial tumor model. On D2 after injection of the tumor cells, the animals receive, subcutaneously, at the tumor site, sodium chloride (control -♦-), 50 μg of PT1 (-Δ-), 100 μg of PT1 (-○-) or 50 μg of IMM (-□-). The volume of the tumor is evaluated every two days. The results are expressed as mean±s.e.m. (Anova Test).

FIG. 4 illustrates the effect of an intratumoral injection of the phosphorothioate oligodeoxynucleotide PT1 or of the phosphodiester oligodeoxynucleotide PE1, both having the SEQ ID NO: 2 (5'-TGACTGTGAACGTTCGAGATGA-3'), in a subcutaneous glial tumor model. On D2 after injection of the tumor cells, the animals receive, subcutaneously, at the tumor site, sodium chloride (control -♦-), 100 μg of PE1 (-□-) or 100 μg of PT1 (-Δ-). The volume of the tumor is evaluated every two days. The results are expressed as mean±s.e.m. (Anova Test).

FIG. 5 illustrates the effect of an intratumoral injection of the phosphorothioate oligodeoxynucleotide PT1 (SEQ ID NO: 2 5'-TGACTGTGAACGTTCGAGATGA-3') or of the phosphorothioate oligodeoxynucleotide IMM (SEQ ID NO: 1 5'-TGACTGTGAAGGTTAGAGATGA-3'), in the neuroblastoma model neuro2a in A/J mice (Sigal R. K. et al. (1991), *J. Pediatr. Surg.* 26 pp 389-96). On D2 after injection of these tumor cells, the animals receive, subcutaneously, at the tumor site, sodium chloride (control -♦-), 50 μg of PT1 (-■-), 100 μg of PT1 (-π-) or 50 μg of IMM(-♦-). The volume of the tumor is evaluated every four days. The results are expressed as mean±s.e.m. (Anova Test).

FIG. 6 illustrates the effect of a subcutaneous or intraperitoneal injection of the phosphorothioate oligodeoxynucleotide PT1 (SEQ ID NO: 2 5'-TGACTGTGAACGTTC-GAGATGA-3'), at the dose of 50 μg, in the neuroblastoma model neuro2a in A/J mice (Sigal R. K. et al. (1991), *J. Pediatr. Surg.* 26 pp 389-96). On D2 after injection of these tumor cells, the animals (n=6 per group) receive 100 μl of sodium chloride (control group -♦-), or 50 μg of PT1 injected i.p. (-■-) or s.c. at a distance from the tumor (-π-), in 100 μl of sodium chloride.

FIG. 7 illustrates the effect of stabilizing an oligonucleotide (SEQ ID NO: 9 5'-TGACTGTGAACGTTATA-GATGA-3') via a linkage of the type phosphorothioate (PT), phosphodiester (PDE), methylphosphonate (MP); phosphodiester stabilized in 3' by a dideoxycytosine base (3') or mixed: phosphodiester with the first 3 linkages in 5' and the last three linkages in 3' of phosphorothioate type (mixed), on the antitumor activity in a subcutaneous glial tumor model. On D2 after injection of the tumor cells, the groups of animals receive, subcutaneously, at the tumor site, sodium chloride (NaCl control, n=9) or 50 μg of the oligonucleotides PT (n=9), PDE (n=8), MP (n=9), 3' (n=7) and mixed (n=9). The volume of the tumor is evaluated on D10. The results are expressed as mean±s.e.m.

FIGS. 8 to 11 illustrate the effect of the sequences 5'-purine-purine-CG-pyrimidine-pyrimidine-$X_1X_2$-3' on the modulation of the antitumor activity in a subcutaneous glial tumor model. On D2 after injection of the tumor cells, the groups of animals (n=6) receive, subcutaneously, at the tumor site, sodium chloride (NaCl control) or 50 μg of the oligonucleotides (SEQ ID NO: 2 to 13). The volume of the tumor is evaluated on D8 (FIGS. 8 to 10) or on D10 (FIG. 11). The results are expressed as mean±s.e.m.:

Figure 10:
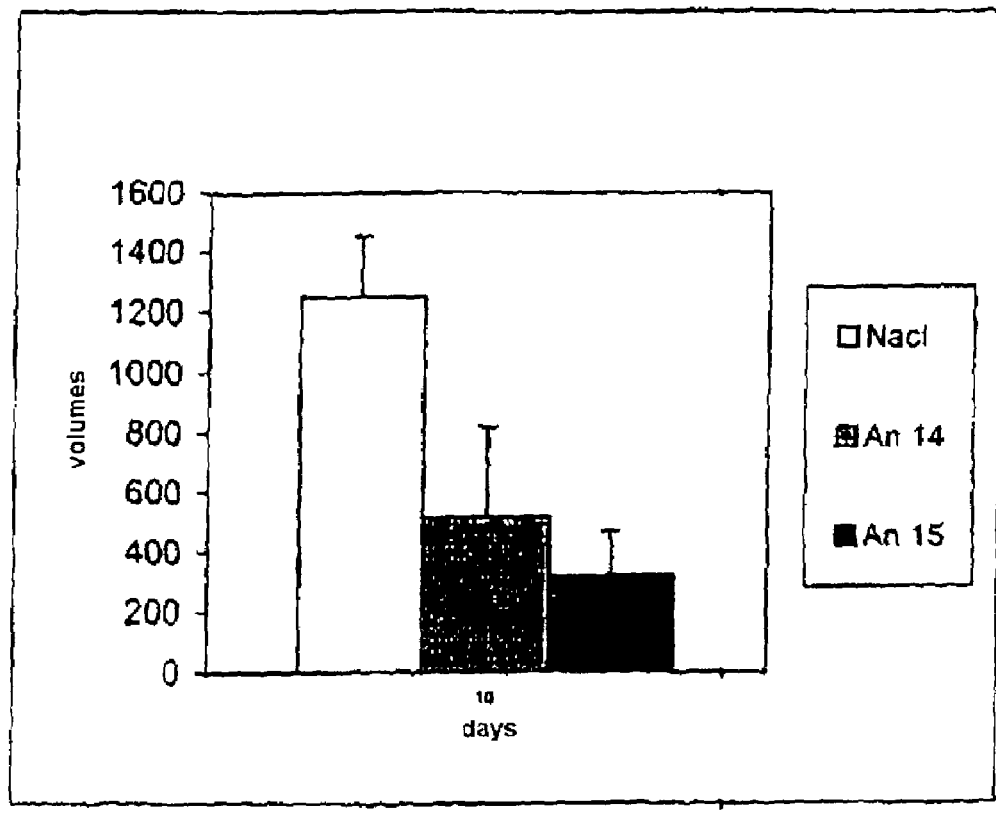

FIG. 10 illustrates the effect of the 2 bases ($X_1X_2$) adjacent to the 3' sequence of the hexameric motif 5'-purine-purine-CG-pyrimidine-pyrimidine-3' on the antitumor effectiveness of the oligonucleotides.

Figure 11:
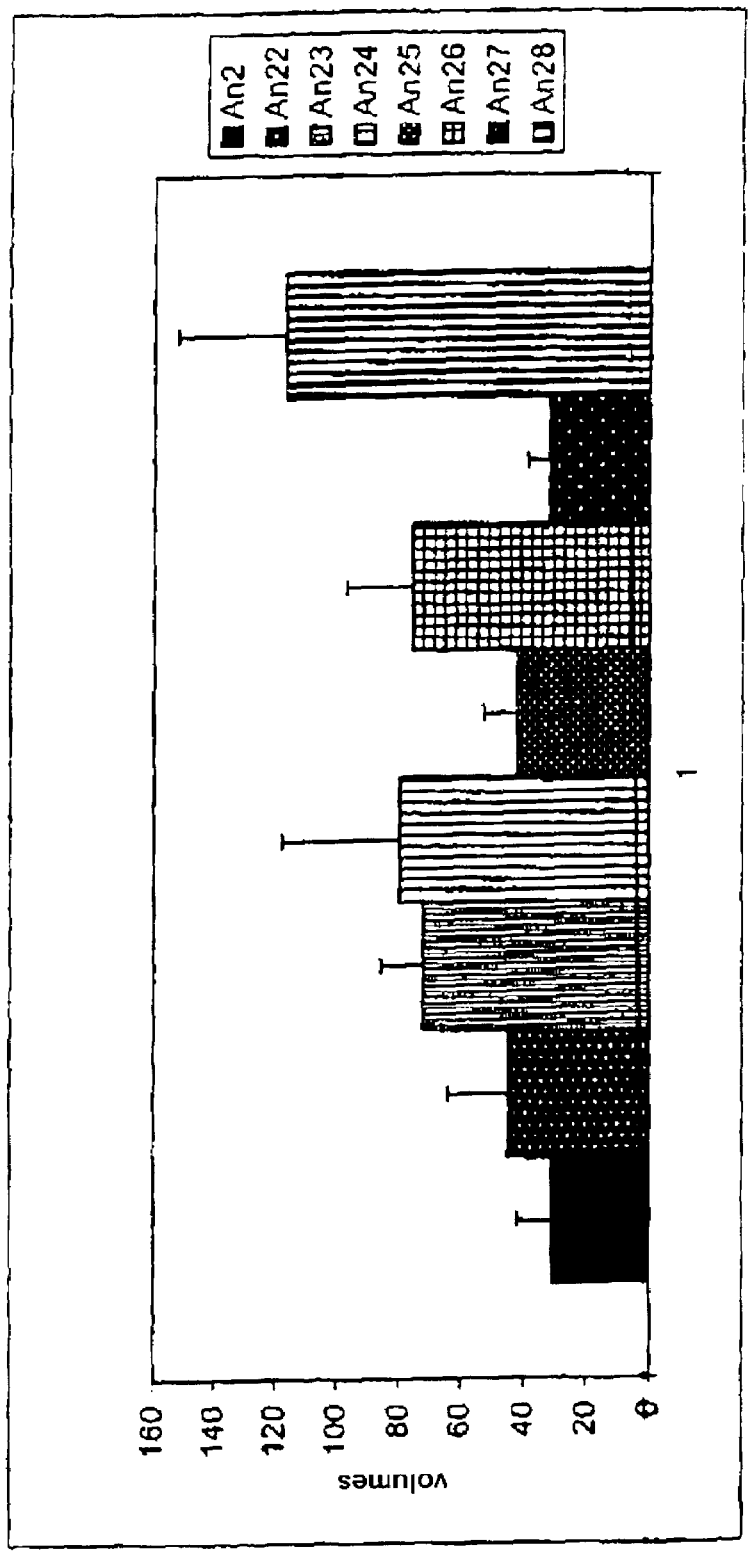

FIG. 11 illustrates the effect of various sequences $X_1X_2$ on the antitumor effectiveness of the oligonucleotides.

The examples which follow illustrate the invention without, however, limiting it to these particular embodiments.

EXAMPLE 1

Effect of an Intratumoral Injection or of an Intraperitoneal Injection of PT1 (SEQ ID NO: 2 5'-TGACTGTGAACGTTCGAGATGA-3') on the Survival of the Animals, in the Glioma Model CNS1 in the Brain of Lewis Rats 1. Procedure:

CNS1 glioma cells cultured in vitro are grafted into the brain of healthy Lewis rats, in a proportion of $10^5$ cells in the right parietal cortex of the rats (Kruse C. A. et al. (1994), J. Neurooncol. 22 pp 191-200).

a) Intratumoral Injection:

50 μg of PT1 in 7 μl of sodium chloride are injected at the tumor site, 1, 5 or 9 days after the graft (group treated on D1, n=6; group treated on D5, n=8; group treated on D9, n=4); a control group (n=14) receives sodium chloride.

b) Intraperitoneal Injection:

50 μg of PT1 are injected intraperitoneally on D1 (n=5); a control group receives sodium chloride (n=5).

Figure 1:
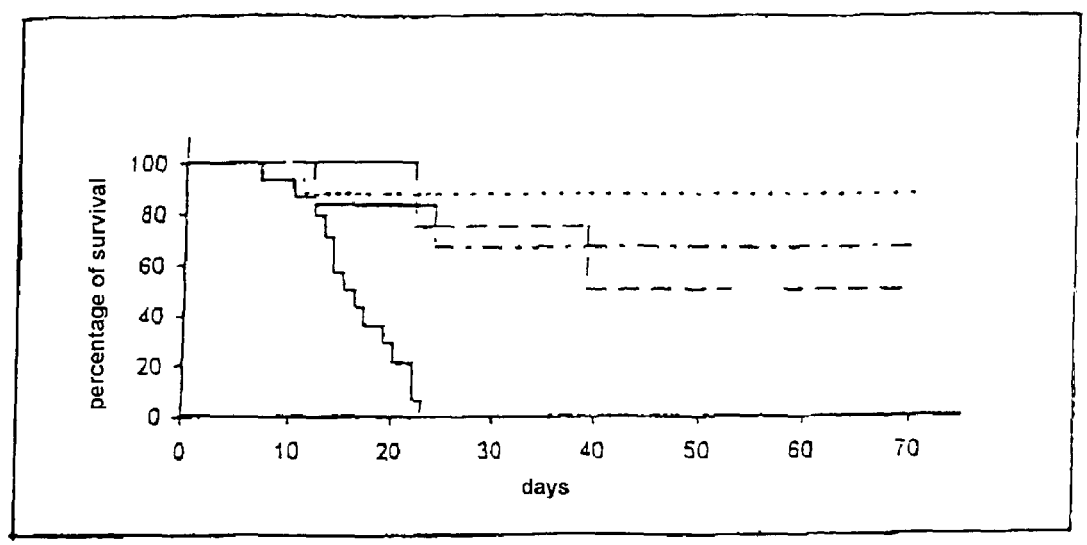

2. Results:

a) Intratumoral Injection:

They are illustrated in FIG. 1.

The control group shows a mean survival of 15 days and all the animals die before the $23^{rd}$ day.

The survival of the animals treated with PT1 is greatly increased, with long-term survivals (>90 days) of 67% (p<0.01), of 88% (p<0.002) and of 50% (p<0.02) for the rats treated on D1, D5 and D9, respectively.

All the dead animals exhibit brain tumors at autopsy.

In the surviving rats, none show neurological symptoms and no tumor is found at autopsy carried out on D90.

The histological study of the brains reveals no inflammatory, demyelinating or toxic lesion in the parenchyma adjacent to the injection site.

b) Intraperitoneal Injection:

Under these conditions, the PT1 has no significant effect.

EXAMPLE 2

Comparison of the Effects of an Intratumoral Injection of PT1 (SEQ ID NO: 2 5'-TGACTGTGAACGTTCGAGATGA-3') on the Survival of the Animals, in the Glioma Model CNS1 of Lewis Rats, with that of an Oligodeoxynucleotide (IMM) Comprising a Non-immunostimulatory Octanucleotide Sequence (SEQ ID NO: 1 5'-TGACTGTGAAGGTTAGAGATGA-3')

1. Procedure:

CNS1 glioma cells cultured in vitro are grafted into the brain of healthy Lewis rats, in a proportion of $10^5$ cells in the right parietal cortex of the rats (Kruse C. A. et al. (1994), *J. Neurooncol.* 22 pp 191-200).

On D1 after the graft carried out under the conditions described in example 1, the rats receive an intratumoral injection of 50 µg of IMM dissolved in 7 µl of sodium chloride, or the vehicle alone (n=5 per group).

2. Results:

The lifespan is not statistically different between the control group, having received the sodium chloride, and the treated group, having received the IMM.

Thus, an oligonucleotide which does not contain any immunostimulatory sequence does not make it possible to increase survival, unlike an oligonucleotide which contains such a sequence (Example 1).

EXAMPLE 3

Effect of an Intratumoral Injection of PT1 (SEQ ID NO: 2 5'-TGACTGTGAACGTTCGAGATGA-3') at Various Doses on the Survival of the Animals, in the Glioma Model CNS1 of Lewis Rats 1. Procedure:

On D1 after the graft carried out under the conditions described in Example 1, the rats receive an intratumoral injection of 1 µg, 10 µg or 50 µg of PT1 dissolved in 7 µl of sodium chloride, or the vehicle alone (n=5 per group).

Figure 2:
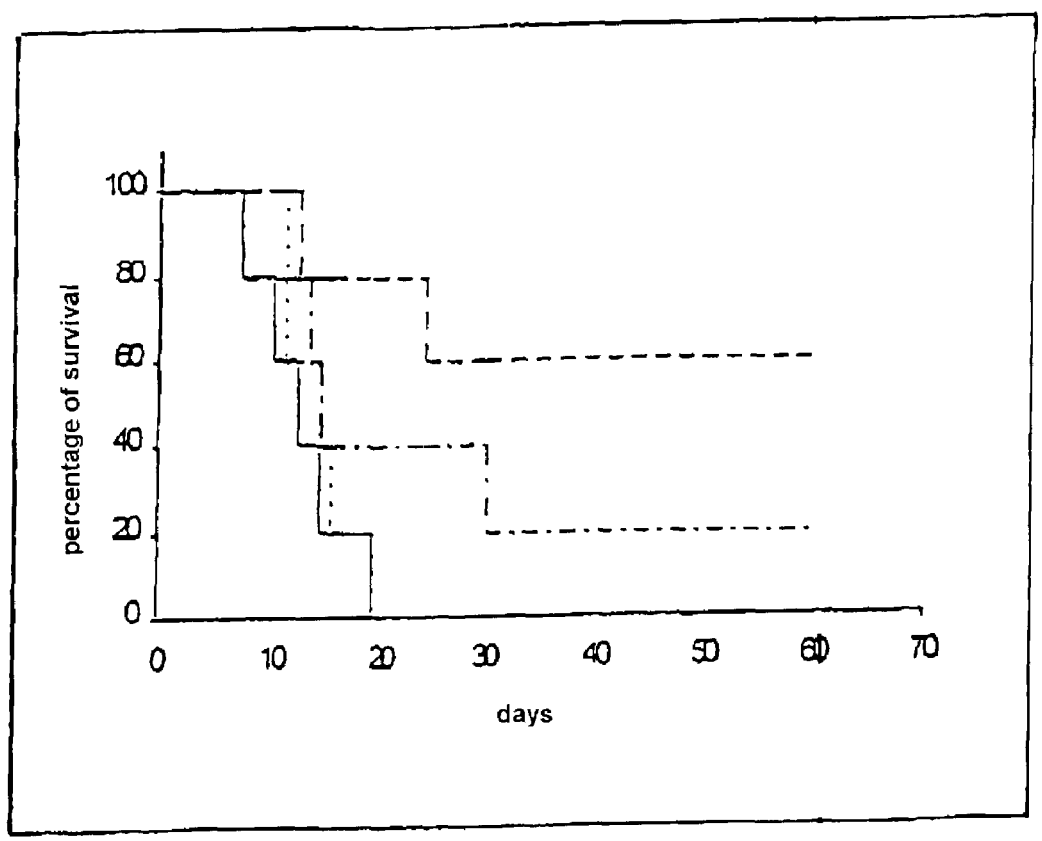

2. Results:

They are illustrated in FIG. 2.

A survival longer than 90 days is obtained in 60% of the cases (p<0.01) after a single injection of 50 µg, and in 20% of the cases (not significant) after a dose of 10 µg.

There is no survivor after a dose of 1 µg (n=5).

All the control rats died.

In the surviving rats, none exhibited neurological symptoms and no tumor is found at autopsy carried out on D90.

EXAMPLE 4

Investigation of the Mechanism of the Effects of PT1 (SEQ ID NO: 2 5'-TGACTGTGAACGTTCGAGATGA-3'), In Vitro and In Vivo, on the CNS1 Glioma Cells 1. Procedure:

a) In Vitro

CNS1 glioma cells are placed in culture on D0. On D1, PT1 at concentrations of 0.05 µM, 0.5 µM and of 5 µM is added to these cells and, on D3, the cells are treated with trypsin and their viability is measured.

b) In Vivo: See Procedure of Example 1.

2. Results:

a) In Vitro

PT1, at concentrations of 0.05 µM, 0.5 µM and of 5 µM has no direct cytotoxic action on the CNS1 cells after culturing for 48 hours.

b) In Vivo

On the other hand, the immunohistochemical studies show that the injection of 50 µg of PT1 in the tumor triggers a massive infiltration of NK cells, of $CD8^+$ T lymphocytes, of macrophages and of microglial cells, whereas the injection of sodium chloride has no effect.

These results suggest that the action of the PT1 is due to activation of the immune system at the tumor site.

EXAMPLE 5

Effect of an Intratumoral Injection of PT1, at a Tumor Site, on the Development of a Tumor Grafted Simultaneously, at a Distance from this Site 1. Procedure:

The tumor cells are grafted under the conditions described in example 1, at two separate sites 4 mm apart.

On D5 after the graft, a group of rats (n=7) receives an intratumoral injection of 50 µg of PT1 dissolved in 7 µl of sodium chloride at just one of these sites, and the control group (n=6) receives the vehicle alone.

2. Results:

All the rats of the control group die within less than 25 days, whereas 44% of the rats of the group treated with PT1 have a prolonged survival (>90 days), (p<0.05).

These results show that the oligonucleotide PT1 has an effect at distance and that the immune response induced at the injection site prevents the development of a tumor grafted simultaneously, at a distance from this site.

EXAMPLE 6

Study of the Immune Memory at 3 Months in the Glioma Model CNS1 of Lewis Rats, After Injection of PT1 (SEQ ID NO: 2 5'-TGACTGTGAACGTTCGAGATGA-3')

1. Procedure:

In rats (n=5) which had been treated with 50 µg of PT1 on D5 after the graft, and which had survived due to this treatment with PT1, a new graft of $10^6$ cells is carried out 12 weeks later, in another site of the cerebral cortex, under the conditions described in example 1. In parallel, a graft of $10^5$ cells is carried out in rats which had not been treated beforehand.

2. Results:

At 90 days, all the animals previously treated with PT1 survived without further treatment.

The histological analysis shows that there is no residual tumor, both for the first site of implantation of the tumor cells and for the second site.

All the control animals died.

These results show that the oligonucleotides have a sustained effect which makes it possible to prevent the development of a tumor, several weeks after the injection of said oligonucleotide. The "memory effect" observed indicates that the oligonucleotide PT1 activates the setting up of a specific antitumor immune response.

EXAMPLE 7

Effect of an Intratumoral Injection of PT1 (SEQ ID NO: 2 5'-TGACTGTGAACGTTCGAGATGA-3') or of an Oligodeoxynucleotide (IMM) Comprising a Nonimmuno-Stimulatory Octanucleotide Sequence (SEQ ID NO: 1 5'-TGACTGTGAAGGTTA-GAGATGA-3'), in a Subcutaneous Glial Tumor Model 1. Procedure:

CNS1 glioma cells cultured in vitro are injected subcutaneously into healthy Lewis rats, in a proportion of $2\times10^6$ cells in the right flank (Kruse C. A. et al. (1994), *J. Neurooncol.* 22 pp 191-200).

This model makes it possible to monitor more accurately the growth of the tumor, which can be easily evaluated every day in the live animal. In this model, 100% of the animals injected develop a tumor which grows for at least 2 weeks.

Next, on D2 after the injection of the tumor cells, 50 μg or 100 μg of PT1, or 50 μg of IMM, in 100 μl of sodium chloride, are injected into the tumor site (group treated with 50 μg of PT1, n=9; group treated with 100 μg of PT1, n=6; group treated with 50 μg of IMM, n=9); a control group (n=9) receives 100 μl of sodium chloride.

The tumor growth is measured every two days and the tumor volume is estimated using the formula:

Vol=(length×width×width×π)/6.

The animals are sacrificed on D12 after the injection of the tumor cells.

Figure 3:
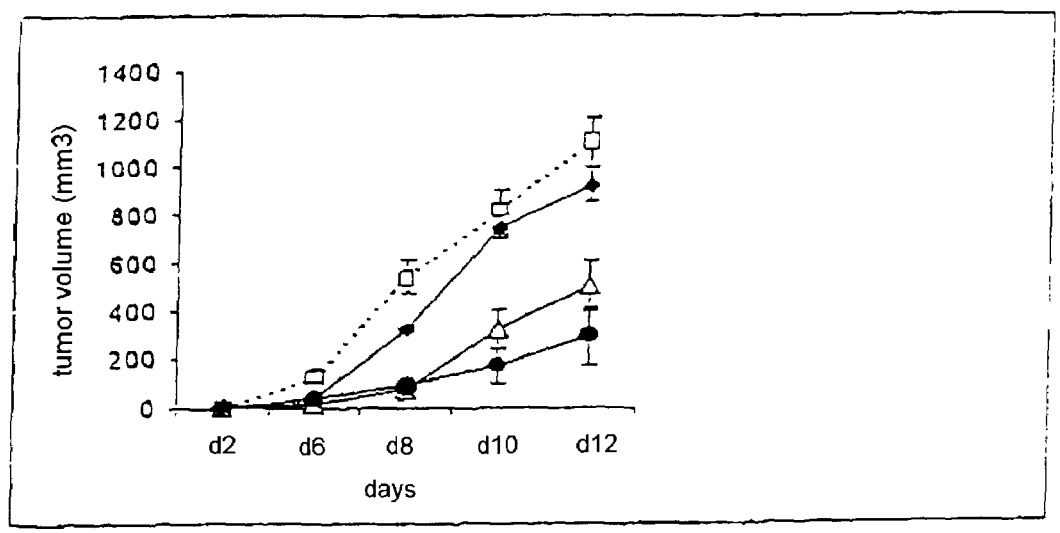

2. Results:

They are illustrated in FIG. 3.

In the control group, 9' animals out of 9 developed a tumor, with a mean tumor volume on D12 of approximately 900 mm$^3$.

In the group treated with IMM, 9 animals out of 9 developed a tumor, with a mean tumor volume on D12 of approximately 1 100 mm$^3$.

In the group treated with 50 μg PT1, 7 animals out of 9 developed a tumor, with a mean tumor volume on D12 of approximately 400 mm$^3$, whereas in the group treated with 100 μg PT1, only 3 animals out of 6 developed a tumor, with a mean tumor volume on D12 of approximately 200 mm$^3$.

This set of results confirms, therefore, that the PT1 had a marked antitumor effect, linked to the presence of an immunostimulatory sequence.

This effect is dose dependent.

EXAMPLE 8

Effect of an Intratumoral Injection of PT1 (Phosphorothioate Oligodeoxynucleotide) or of PE1 (Non-Stabilized Oligodeoxynucleotide) in a Subcutaneous Glial Tumor Model; PT1 and PE1 Both Having the Same Immunostimulatory Sequence (SEQ ID NO: 2 5'-TGACTGTGAACGTTCGAGATGA-3')

1. Procedure:

CNS1 glioma cells cultured in vitro are injected subcutaneously into healthy Lewis rats, in a proportion of $2\times10^6$ cells in the right flank, under the conditions described in example 7.

Next, on D2 after the injection of the tumor cells, 100 μg of PT1 or 100 μg of PE1 are injected into the tumor site (group treated with 100 μg of PT1 in 100 μl of sodium chloride, n=6; group treated with 100 μg of PE1 in 100 μl of sodium chloride, n=6); a control group (n=6) receives 100 μl of sodium chloride.

The tumor growth is measured every two days and the tumor volume is measured as described in Example 7.

The animals are sacrificed on D12 after the injection of the tumor cells.

Figure 4:
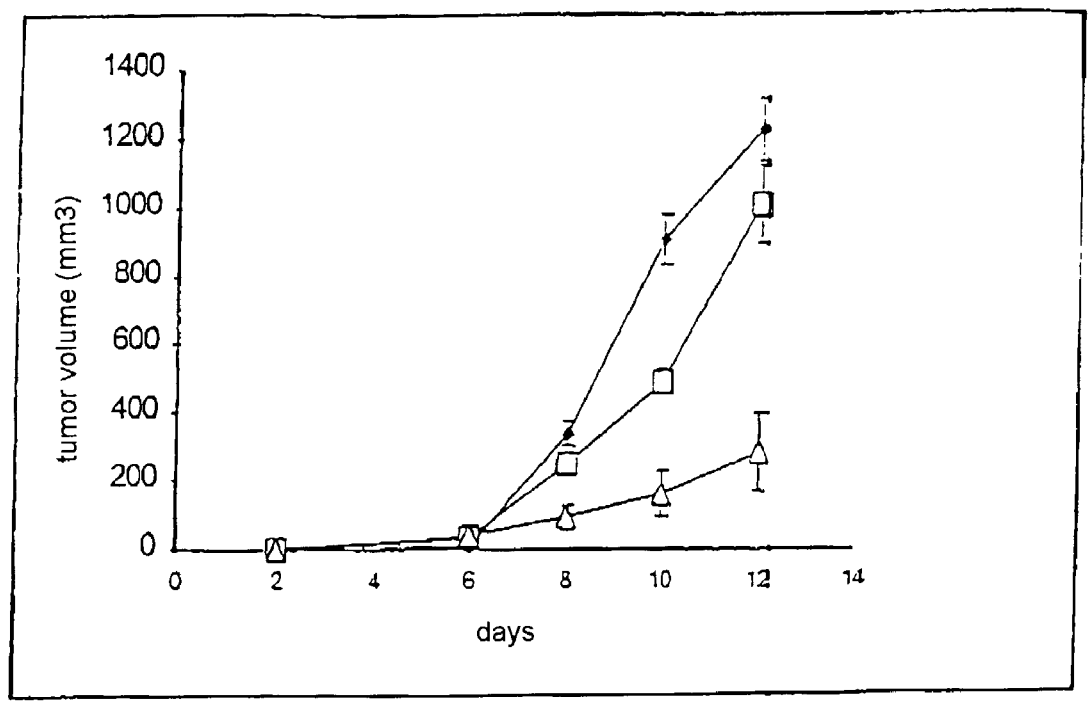

2. Results:

They are illustrated in FIG. 4.

In the control group, 6 animals out of 6 developed a tumor, with a mean tumor volume on D12 of approximately 1 200 mm$^3$.

In the group treated with PE1, 6 animals out of 6 developed a tumor, with a mean tumor volume on D12 of approximately 1 000 mm$^3$.

In the group treated with 100 μg PT1, only 3 animals out of 6 developed a tumor, with a mean tumor volume on D12 of approximately 200 mm$^3$.

EXAMPLE 9

Effect of an Intratumoral Injection of PT1 (SEQ ID NO: 2 5'-TGACTGTGAACGTTCGAGATGA-3') and of IMM (SEQ ID NO: 1 5'-TGACTGTGAAG-GTTAGAGATGA-3') in the Neuroblastoma Model Neuro2a in A/J Mice 1. Procedure:

The tumor is obtained by injecting one million neuro2a cells into the right flank of A/J mice (Sigal R. K. et al. (1991), *J. Pediatr. Surg.*, 26 pp 389-96). This tumor grows in 15-20 days, generally resulting in the death of the animal or making it necessary to sacrifice it.

On D2 after the injection of these tumor cells, 50 μg or 100 μg of PT1, or 50 μg of IMM, in 100 μl of sodium chloride, or 100 μl of sodium chloride (control group), are injected into the same site (n=6 animals per group).

The tumor growth is measured every four days and the tumor volume is measured as indicated in example 7.

The animals are sacrificed on D22 after the injection of these tumor cells.

Figure 5:
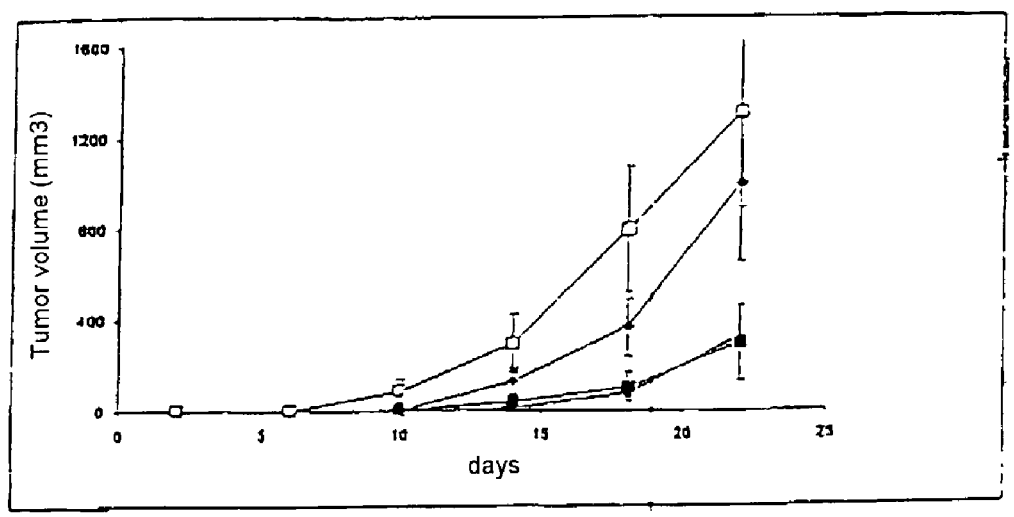

2. Results:

They are illustrated in FIG. 5.

In this model, the mean tumor volume on D22 is approximately 800 mm$^3$ in the control group, approximately 1200 mm$^3$ in the group treated with 50 μg of IMM, and approximately 200 mm$^3$ in the groups treated with 50 μg or 100 μg of PT1.

EXAMPLE 10

Effect of a Subcutaneous or Intraperitoneal Injection of PT1 (SEQ ID NO: 2 5'-TGACTGTGAACGTTCGAGATGA-3') at the Dose of 50 µg, in the Neuroblastoma Model Neuro2a in A/J Mice 1. Procedure:

The tumor is obtained according to the procedure described in example 9.

On D2 after the injection of the tumor cells, 50 µg of PT1 in 100 µl of sodium chloride, or 100 µl of sodium chloride (control group), are injected either subcutaneously at a distance from the tumor, or intraperitoneally (n=6 animals per group).

The tumor growth is measured every four days and the tumor volume is measured as indicated in example 7.

The animals are sacrificed on D22 after the injection of the tumor cells.

Figure 6:
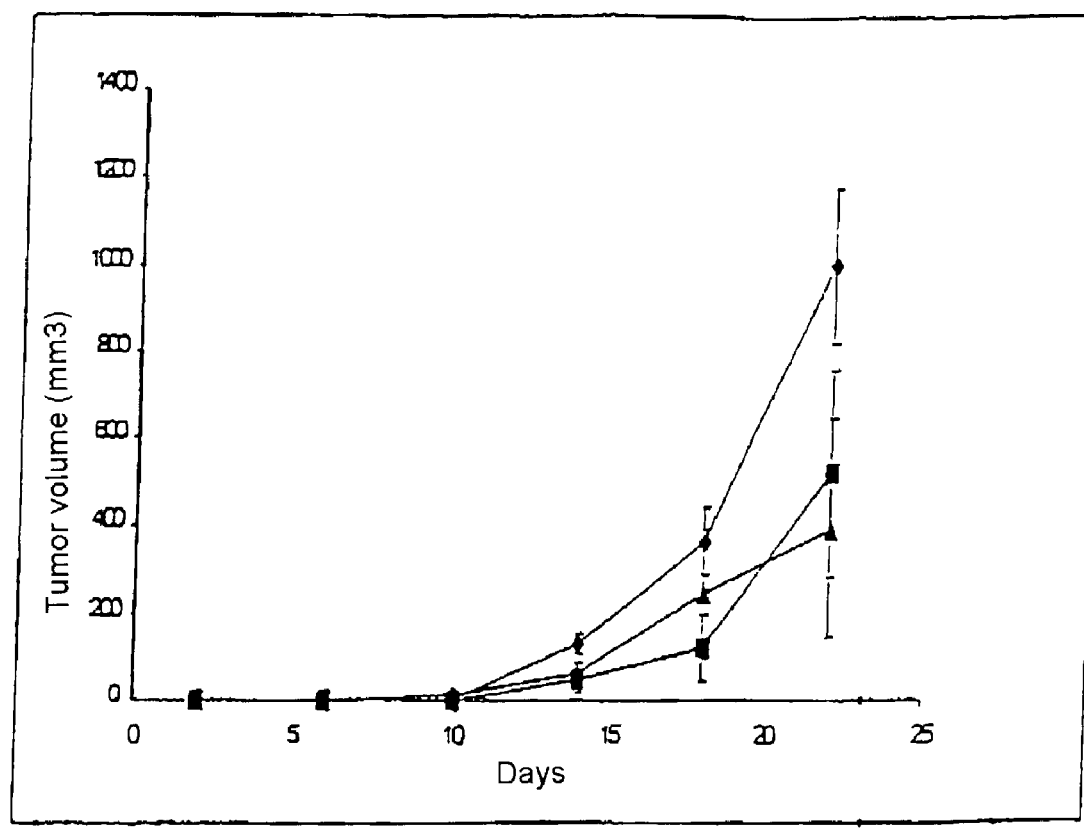

2. Results:

They are illustrated in FIG. 6.

In this model, the mean tumor volume on D22 is approximately 1 000 $mm^3$ in the control group, approximately 400 $mm^3$ in the group treated with 50 µg of PT1 injected subcutaneously and approximately 500 $\mu m^3$ in the group treated with 50 µg of PT1 injected intraperitoneally.

EXAMPLE 11

Effect of Repeated Subcutaneous Injection of PT1 (SEQ ID NO: 2 5'-TGACTGTGAACGTTC-GAGATGA-3') or of IMM (SEQ ID NO: 1 5'-TGACTGTGAAGGTTAGAGATGA-3') at the Dose of 10 µg, for 15 Days, in the Neuroblastoma Model Neuro2a in A/J Mice 1. Procedure:

The tumor is obtained according to the procedure described in Example 9.

The tumor growth is measured regularly in all the animals, and when the diameter of the tumor reaches 5 mm, PT1 is injected subcutaneously, around the tumor, for 15 days, at the dose of 10 µg per day in 100 µl of sodium chloride (group treated with PT1, n=7) or IMM is injected subcutaneously, around the tumor, for 15 days, at the dose of 10 µg per day in 100 µl of sodium chloride (group treated with IMM, n=4) or 100l of sodium chloride is injected subcutaneously, around the tumor, for 15 days (control group, n=6).

2. Results:

In the control group and in the group treated with the IMM, the tumor growth is not slowed down and all the animals of these two groups die from their tumor.

In the group treated with PT1, complete disappearance of the tumor, with no long term recurrence, is observed in 3 mice; in 3 others, the tumors are stabilized for 3 weeks but then recommence their progression until the animals die.

These results show that the stabilized immunostimulatory oligonucleotides used according to the invention have a marked intrinsic antitumor effect, linked to the presence of the immunostimulatory sequence and to their stabilization.

EXAMPLE 12

Effect of Stabilizing an Oligonucleotide (SEQ ID NO: 9 5'-TGACTGTGAACGTTATAGATGA-3') on the Antitumor Activity, in a Subcutaneous Glial Tumor Model 1. Procedure:

CNS1 glioma cells cultured in vitro are injected subcutaneously into healthy Lewis rats, in a proportion of $2 \times 10^6$ cells in the right flank (Kruse C. A. et al. (1994), *J. Neurooncol.* 22 pp 191-200).

On D2 after the injection of the tumor cells, 50 µg of the oligonucleotides having the various chemical linkages are injected into the tumor site and the tumor volume is measured on D10 (groups treated with an oligonucleotide of linkage: phosphorothioate (PT, n=9), phosphodiester (PDE, n=8), methylphosphonate (MP, n=9), phosphodiester stabilized in 3' by a dideoxycytosine base (group 3', n=7), or mixed: phosphodiester with the first three linkages in 5' and the last three linkages in 3' of the phosphorothioate type (mixed group, n=9). The control group receives 100 µl of sodium chloride (NaCl n=9).

Figure 7:
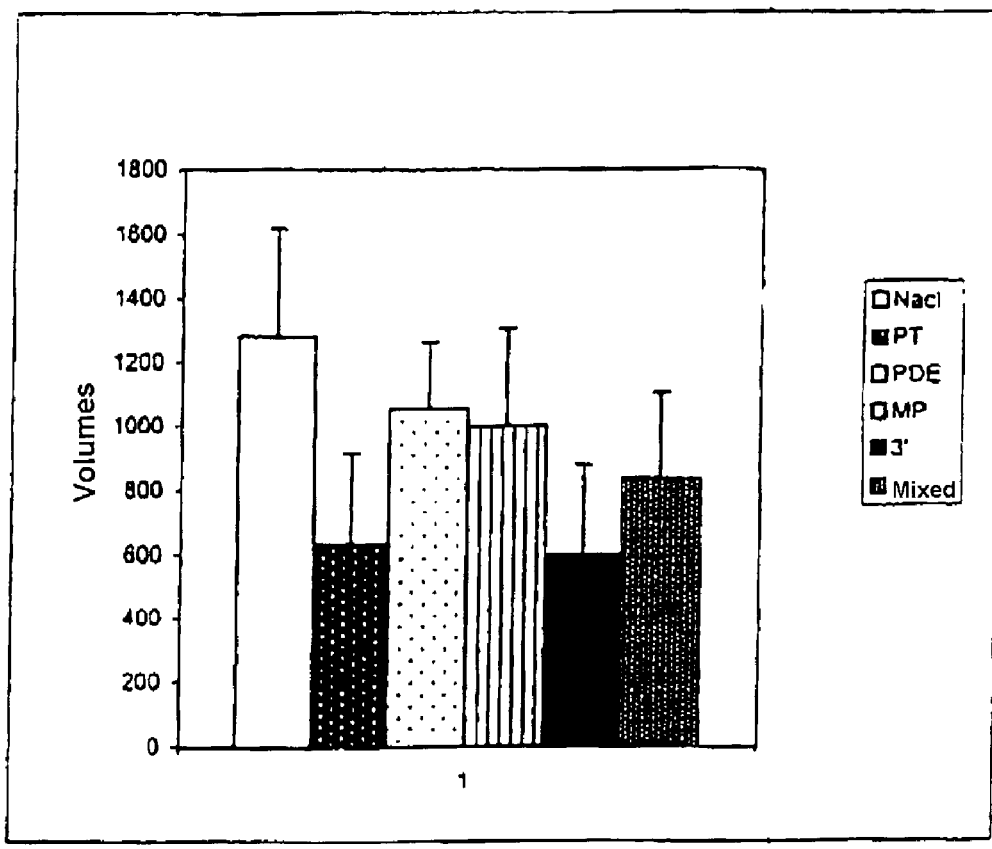

2. Results:

They are illustrated in FIG. 7.

In this model, the most effective ODNs are the oligonucleotides of type phosphorothioate, stabilized in 3', or mixed, with a decrease in the tumor volume of 50%, 53% and 34%, respectively, with respect to the volume of the controls.

EXAMPLE 13

Effect of the Sequences 5'-Purine-Purine-CG-Pyrimidine-Pyrimidine-$X_1X_2$-3' on the Modulation of the Antitumor Activity 1. Procedure:

CNS1 glioma cells cultured in vitro are injected subcutaneously into healthy Lewis rats, in a proportion of $2 \times 10^6$ cells in the right flank (Kruse C. A. et al. (1994), *J. Neurooncol.* 22 pp 191-200).

On D2 after the injection of the tumor cells, 50 µg of the various oligonucleotides (SEQ ID NO: 2 to 13) are injected into the tumor site and the tumor volume is measured on D10 (FIGS. 8 to 10) or on D8 (FIG. 11).

2. Results:

2.1. Effect of the Oligonucleotide Sequence on the Antitumor Effectiveness

Figure 8:
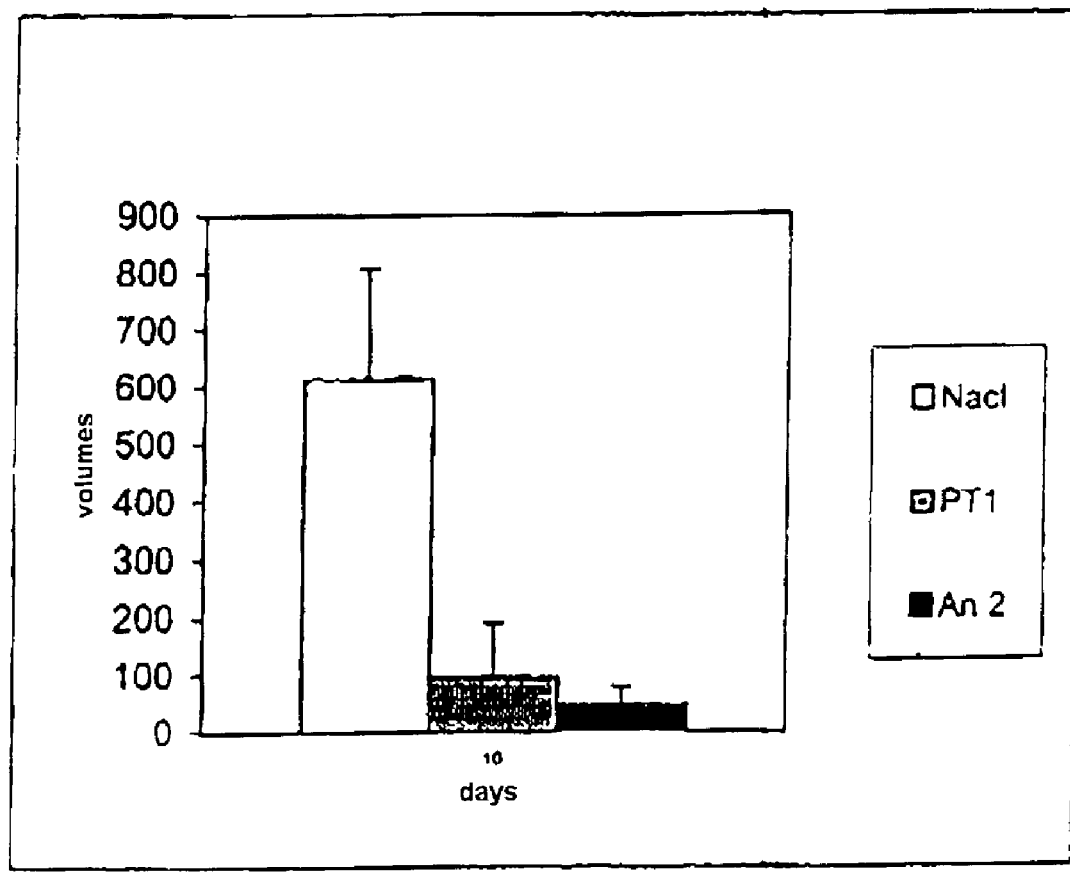
FIG. 8 illustrates the effect of the oligonucleotide sequences on the antitumor effectiveness.

The results are illustrated in FIG. 8.

The oligonucleotide PT1 (SEQ ID NO: 2 5'-TGACTGT-GAACGTTCGAGATGA-3') used above (examples 1 to 10) is less effective than the oligonucleotide An 2 (SEQ ID NO: 8 5'-TGCCAGTGACGTCATGTGAC-3').

The difference in effectiveness of these two oligonucleotides is linked either to the sequence of the hexameric motif 5'-purine-purine-CG-pyrimidine-pyrimidine-3' comprising the nonmethylated CG motif (underlined sequence), or to the sequences adjacent to this motif.

2.2. Effect of the Sequence of the Hexameric Motif 5'-Purine-Purine-CG-Pyrimidine-Pyrimidine-3' and of the Adjacent Sequences on the Antitumor Effectiveness of the Oligonucleotides.

Figure 9:
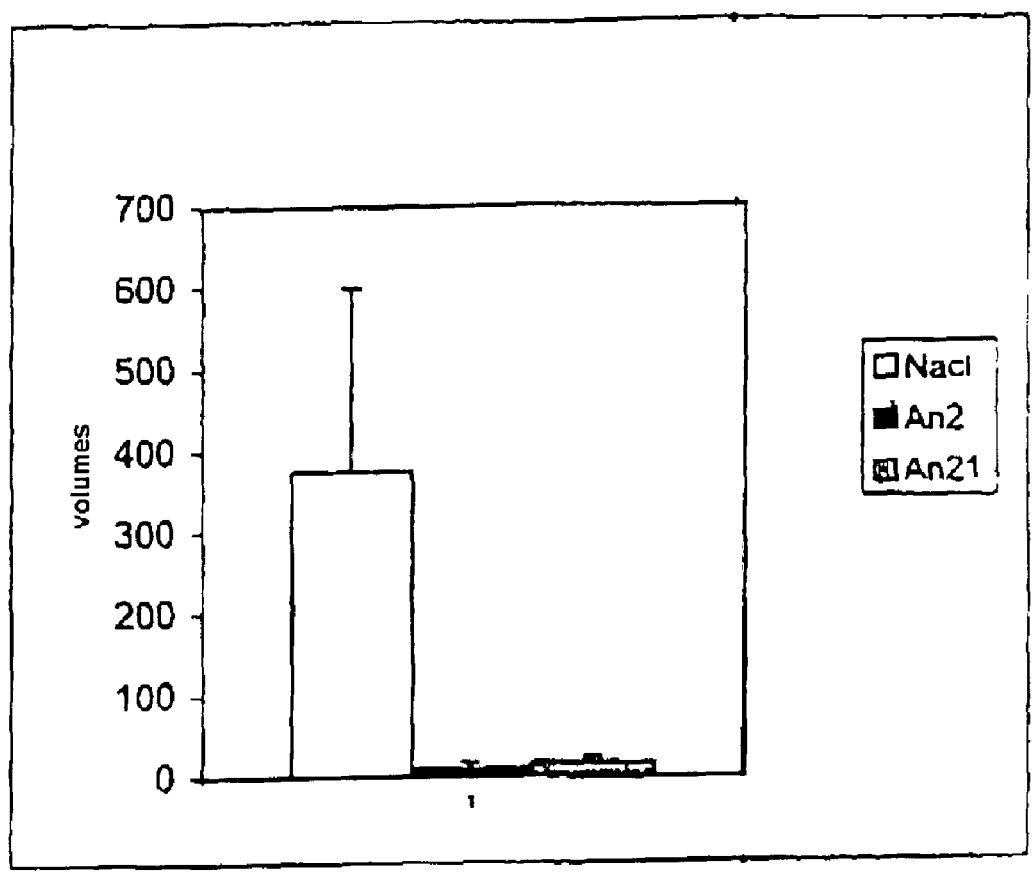
FIG. 9 illustrates the effect of the sequence of the hexameric motif 5'-purine-purine-CG-pyrimidine-pyrimidine-3' and of the adjacent sequences on the antitumor effectiveness of the oligonucleotides.

The results are illustrated in FIG. 9.

They show that oligonucleotides having a different hexameric motif, GACGTC (An2, SEQ ID NO: 8 5'-TGCCAGT-GACGTCATGTGAC-3') or AACGTT (An21, SEQ ID NO: 10 5'-TGCCAGTAACGTTATGTGAC-3'), and identical adjacent sequences have the same antitumor effectiveness.

Consequently, the differences in effectiveness observed, in example 2.1, between the oligonucleotides PT1 and An2 are linked to the nature of the sequences adjacent to the hexameric motif. The optimum antitumor sequences are found in the adjacent sequences of the oligonucleotide An2.

2.3. Effect of the 2 Bases ($X_1X_2$) Adjacent to the 3' Sequence of the Hexameric Motif 5'-Purine-Purine-CG-Pyrimidine-Pyrimidine-3' on the Antitumor Effectiveness The results are illustrated in FIG. 10.

They show that the 2 bases adjacent to the 3' sequence of the hexameric motif modulate, all by themselves, the effectiveness of the oligonucleotides, since 2 oligonucleotides which are identical along their entire sequence with the exception of these 2 nucleotides have different effectivenesses, of the order of those previously observed with the oligonucleotides of example 2.1. Thus, the oligonucleotide An 14 (SEQ ID NO: 3 5'-TGACTGTGAACGTTCCA-GATGA-3') is less effective than the oligonucleotide An 15 (SEQ ID NO: 9, 5'-TGACTGTGAACGTTATAGATGA-3'). The nucleotides AT positioned 3' of the hexameric motif (An2 (FIG. 8) and An 15 (FIG. 10)) make it possible to increase the antitumor effectiveness, whereas the nucleotides CC (An 14, FIG. 10) and CG (PT1, FIG. 8) have less marked antitumor effects.

2.4. Effect of Various Sequences $X_1X_2$ on the Antitumor Effectiveness

The results are illustrated in FIG. 11.

The optimum antitumor effect is observed with the sequences $X_1X_2$=AT, AA, CT or TT (An2 SEQ ID NO: 8 5'-TGCCAGTAACGTTAAGTGAC-3'; An22 SEQ ID NO: 11 5'-TGCCAGTAACGTTAAGTGAC-3'; An25 SEQ ID NO: 12 5'-TGCCAGTAACGTCTGTGAC-3'; An27 SEQ ID NO: 13 5'-TGCCAGTAACGTTTTGTGAC-3').

The sequences $X_1X_2$=AC, AG, GT and CC and CG (An23 SEQ ID NO: 4 5'-TGCCAGTAACGTTACGTGAC-3'; An24 SEQ ID NO: 5 5'-TGCCAGTAACGTTAGGTGAC-3'; An26 SEQ ID NO: 6 5'-TGCCAGTAACGTTGTGTGAC-3'; An 28 SEQ ID NO: 7 5'-TGCCAGTAACGTTCCGTGAC-3' and PT1 SEQ ID NO: 2 5'-TGACTGTGAACGTTCGAGATGA-3' (see FIG. 8)) do not improve the antitumor activity of the oligonucleotides having a hexameric motif 5'-purine-purine-CG-pyrimidine-pyrimidine-3'.

These results show that the set of stabilized oligonucleotides of the type 5'-purine-purine-CG-pyrimidine-pyrimidine-$X_1X_2$-3' with $X_1X_2$=AA, AT, CT or TT has optimized antitumor activity.

The invention claimed is:

1. A stabilized oligodeoxyribonucleotide that consists of 20 to 100 nucleotides when single-stranded, or 20 to 100 base-pairs when double-stranded, which stabilized oligodeoxyribonucleotide contains at least one nonmethylated octameric CG motif of the sequence AACGTTAT (nucleotides 9-16 of SEQ ID NO: 9);

wherein said stabilized oligodeoxyribonucleotide is chemically modified and resistant to degradation by nucleases in the human body compared to the corresponding unmodified, oligodeoxyribonucleotide in a natural form that is sensitive to the nucleases in the human body.

2. The stabilized oligodeoxyribonucleotide of claim 1 that is stabilized by a modified backbone selected from the group consisting of a phosphorothioate, a phosphorodithioate, a phosphodiester-phosphorothioate mixture, a methylphosphonate, and a stabilization at a 3' or 5' end.

3. The stabilized oligodeoxyribonucleotide of claim 1, wherein the cytosine in said motif is replaced with 5-bromocytosine.

4. A composition comprising the stabilized oligodeoxyribonucleotide of claim 1 and a pharmaceutically acceptable carrier or excipient.

5. A method for treating a tumor comprising intratumoral administration of an effective amount of the stabilized oligodeoxyribonucleotide of claim 1 to a subject in need thereof.

6. The stabilized oligodeoxyribonucleotide of claim 1 which is single-stranded.

7. The stabilized oligodeoxyribonucleotide of claim 1 which is double-stranded.

8. The stabilized oligodeoxyribonucleotide of claim 1 that contains several nonmethylated octameric CG motifs of the sequence AACGTTAT (nucleotides 9-16 of SEQ ID NO: 9).

9. The stabilized oligodeoxyribonucleotide of claim 1 that contains two or three nonmethylated octameric CG motifs of the sequence AACGTTAT (nucleotides 9-16 of SEQ ID NO: 9).

10. A stabilized oligodeoxyribonucleotide that consists of 20 to 100 nucleotides when single-stranded, or 20 to 100 base-pairs when double-stranded, which stabilized oligonucleotide contains at least one nonmethylated octameric CG motif of the sequence AACGTTAT (nucleotides 9-16 of SEQ ID NO: 9), and has a sequence selected from the group consisting of SEQ ID NO: 9, 10, 16, 21, 31, 33, 34 and 35.

11. The composition of claim 4, comprising an encapsulating agent.

12. The composition of claim 4, comprising a colloidal dispersion system.

13. The composition of claim 4, wherein the oligodeoxyribonucleotide is coupled to a molecule that increases the affinity of the composition to a tumor.

14. The composition of claim 4, wherein the oligodeoxyribonucleotide is coupled to an antibody specific for tumor tissue.

15. The method of claim 5, wherein said subject is human.

16. The method of claim 5, wherein the tumor is located in the central or peripheral nervous system.

17. The method of claim 5, wherein the tumor is selected from the group consisting of astrocytomas, glioblastomas, medulloblastomas, neuroblastomas, melanomas and carcinomas.

* * * * *

```
                      SEQUENCE LISTING

<160> NUMBER OF SEQ ID NOS: 48

<210> SEQ ID NO 1
<211> LENGTH: 22
<212> TYPE: DNA
<213> ORGANISM: Artificial sequence
<220> FEATURE:
<223> OTHER INFORMATION: Oligodeoxynucleotide

<400> SEQUENCE: 1
tgactgtgaa ggttagagat ga                                              22

<210> SEQ ID NO 2
<211> LENGTH: 22
<212> TYPE: DNA
<213> ORGANISM: Artificial sequence
<220> FEATURE:
<223> OTHER INFORMATION: Oligodeoxynucleotide

<400> SEQUENCE: 2
tgactgtgaa cgttcgagat ga                                              22

<210> SEQ ID NO 3
<211> LENGTH: 22
<212> TYPE: DNA
<213> ORGANISM: Artificial sequence
<220> FEATURE:
<223> OTHER INFORMATION: Oligodeoxynucleotide

<400> SEQUENCE: 3
tgactgtgaa cgttccagat ga                                              22

<210> SEQ ID NO 4
<211> LENGTH: 20
<212> TYPE: DNA
<213> ORGANISM: Artificial sequence
```

```
<220> FEATURE:
<223> OTHER INFORMATION: Oligodeoxynucleotide

<400> SEQUENCE: 4
tgccagtaac gttacgtgac                                               20

<210> SEQ ID NO 5
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 5
tgccagtaac gttaggtgac                                               20

<210> SEQ ID NO 6
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 6
tgccagtaac gttgtgtgac                                               20

<210> SEQ ID NO 7
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 7
tgccagtaac gttccgtgac                                               20

<210> SEQ ID NO 8
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 8
tgccagtgac gtcatgtgac                                               20

<210> SEQ ID NO 9
<211> LENGTH: 22
<212> TYPE: DNA
<213> ORGANISM: Artificial sequence
<220> FEATURE:
<223> OTHER INFORMATION: Oligodeoxynucleotide

<400> SEQUENCE: 9
tgactgtgaa cgttatagat ga                                            22

<210> SEQ ID NO 10
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 10
tgccagtaac gttatgtgac                                               20
```

<210> SEQ ID NO 11
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 11
tgccagtaac gttaagtgac                                          20

<210> SEQ ID NO 12
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 12
tgccagtaac gttctgtgac                                          20

<210> SEQ ID NO 13
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 13
tgccagtaac gttttgtgac                                          20

<210> SEQ ID NO 14
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 14
gtatgacgac gtcatctagc                                          20

<210> SEQ ID NO 15
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 15
tactgcagac gtcattatgc                                          20

<210> SEQ ID NO 16
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 16
ataacgttat gtaacgttat                                          20

<210> SEQ ID NO 17
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 17
atgacgtcat gtgacgtcat         20

<210> SEQ ID NO 18
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 18
atgacgtcat gtaacgttat         20

<210> SEQ ID NO 19
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 19
tgaacgttat tgaacgttat         20

<210> SEQ ID NO 20
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 20
tggacgtcat tggacgtcat         20

<210> SEQ ID NO 21
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 21
tggacgtcat tgaacgttat         20

<210> SEQ ID NO 22
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 22
aggacgtcaa tgaacgttaa         20

<210> SEQ ID NO 23
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 23
agaacgttaa tgaacgttaa         20

<210> SEQ ID NO 24

-continued

```
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 24
aggacgtcaa tggacgtcaa                                           20

<210> SEQ ID NO 25
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 25
aggacgtctt gtaacgtttt                                           20

<210> SEQ ID NO 26
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 26
agaacgtttt gtaacgtttt                                           20

<210> SEQ ID NO 27
<211> LENGTH: 19
<212> TYPE: DNA
<213> ORGANISM: Artificial sequence
<220> FEATURE:
<223> OTHER INFORMATION: Oligodeoxynucleotide

<400> SEQUENCE: 27
aggacgtctt gtgacgttt                                            19

<210> SEQ ID NO 28
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 28
ttgacgtcct ttaacgttct                                           20

<210> SEQ ID NO 29
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 29
ttaacgttct ttaacgttct                                           20

<210> SEQ ID NO 30
<211> LENGTH: 20
<212> TYPE: DNA
<213> ORGANISM: Artificial sequence
<220> FEATURE:
<223> OTHER INFORMATION: Oligodeoxynucleotide

<400> SEQUENCE: 30
```
ttgacgtcct ttgacgtcct                              20

<210> SEQ ID NO 31
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 31
taaacgttat aacgttataa cgttat                       26

<210> SEQ ID NO 32
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 32
tagacgtcat gacgtcatga cgtcat                       26

<210> SEQ ID NO 33
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 33
taaacgttat aacgttatga cgtcat                       26

<210> SEQ ID NO 34
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 34
taaacgttat gacgtcatga cgtcat                       26

<210> SEQ ID NO 35
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 35
tagacgtcat aacgttataa cgttat                       26

<210> SEQ ID NO 36
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 36
taaacgttaa aacgttaaaa cgttaa                       26

<210> SEQ ID NO 37
<211> LENGTH: 26
<212> TYPE: DNA

```
<213> ORGANISM: Artificial sequence
<220> FEATURE:
<223> OTHER INFORMATION: Oligodeoxynucleotide

<400> SEQUENCE: 37
tagacgtcaa gacgtcaaga cgtcaa                                              26

<210> SEQ ID NO 38
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 38
taaacgttaa aacgttaaga cgtcaa                                              26

<210> SEQ ID NO 39
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 39
taaacgttaa gacgtcaaga cgtcaa                                              26

<210> SEQ ID NO 40
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 40
tagacgtcaa aacgttaaaa cgttaa                                              26

<210> SEQ ID NO 41
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 41
taaacgttct aacgttctaa cgttct                                              26

<210> SEQ ID NO 42
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 42
tagacgtcct gacgtcctga cgtcct                                              26

<210> SEQ ID NO 43
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 43
taaacgttct aacgttctga cgtcct                                              26
```

```
<210> SEQ ID NO 44
<211> LENGTH: 28
<212> TYPE: DNA
<213> ORGANISM: Artificial sequence
<220> FEATURE:
<223> OTHER INFORMATION: Oligodeoxynucleotide

<400> SEQUENCE: 44
taaacgtttt aaacgtttta aacgtttt                                         28

<210> SEQ ID NO 45
<211> LENGTH: 28
<212> TYPE: DNA
<213> ORGANISM: Artificial sequence
<220> FEATURE:
<223> OTHER INFORMATION: Oligodeoxynucleotide

<400> SEQUENCE: 45
tagacgtctt agacgtctta gacgtctt                                         28

<210> SEQ ID NO 46
<211> LENGTH: 28
<212> TYPE: DNA
<213> ORGANISM: Artificial sequence
<220> FEATURE:
<223> OTHER INFORMATION: Oligodeoxynucleotide

<400> SEQUENCE: 46
taaacgtttt aaacgtttta gacgtctt                                         28

<210> SEQ ID NO 47
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 47
tcaacgttat aacgttataa cgttat                                           26

<210> SEQ ID NO 48
<211> LENGTH: 26
<212> TYPE: DNA
<213> ORGANISM: Artificial sequence
<220> FEATURE:
<223> OTHER INFORMATION: Oligodeoxynucleotide

<400> SEQUENCE: 48
tcgacgtcat gacgtcatga cgtcat                                           26
```